(12) United States Patent
Lee et al.

(10) Patent No.: US 10,758,906 B2
(45) Date of Patent: Sep. 1, 2020

(54) CELL SEPARATION CHIP AND SYSTEM (71) Applicant: GENOBIO, INC., Seoul (KR)

(72) Inventors: Jea Ku Lee, Gwangmyeong-si (KR); Ju Hyun Hwang, Seoul (KR); Sung Hoon Park, Seoul (KR); Jong Jin Jo, Gwangmyeong-si (KR)

(73) Assignee: GENOBIO, INC., Seoul (KR)

( * ) Notice: Subject to any disclaimer, the term of this patent is extended or adjusted under 35 U.S.C. 154(b) by 185 days.

(21) Appl. No.: 15/999,665

(22) PCT Filed: Dec. 29, 2016

(86) PCT No.: PCT/KR2016/015502
§ 371 (c)(1),
(2) Date: Aug. 20, 2018

(87) PCT Pub. No.: WO2017/142190
PCT Pub. Date: Aug. 24, 2017

(65) Prior Publication Data
US 2019/0255528 A1    Aug. 22, 2019

(30) Foreign Application Priority Data

Feb. 18, 2016 (KR) .................. 10-2016-0019173
Dec. 29, 2016 (KR) .................. 10-2016-0182071

(51) Int. Cl.
*B01L 3/00* (2006.01)
*G01N 33/574* (2006.01)
(Continued)

(52) U.S. Cl.
CPC ... *B01L 3/502776* (2013.01); *B01L 3/502761* (2013.01); *G01N 33/574* (2013.01);
(Continued)

(58) Field of Classification Search
CPC ..... B01L 2200/0652; B01L 2300/0816; B01L 2300/0864; B01L 2300/087;
(Continued)

(56) References Cited

U.S. PATENT DOCUMENTS

2004/0029258 A1    2/2004    Heaney et al.
2007/0166195 A1    7/2007    Padmanabhan et al.
(Continued)

FOREIGN PATENT DOCUMENTS

EP    2191895 A1    6/2010
JP    2008082772 A   4/2008
(Continued)

OTHER PUBLICATIONS

The extended European search report of 16890780.6, dated Jul. 30, 2019.
(Continued)

*Primary Examiner* — Jennifer Wecker
(74) *Attorney, Agent, or Firm* — STIP Law Group, LLC (57) ABSTRACT

The present invention relates to a system and method for cell separation. The system includes: a cartridge having a polygonal shape in cross section and including an injection part, a separation chip separating a flow channel of a sample injected through the injection part, and a discharge part; and a base plate coupled to the cartridge through its upper surface and including a magnetic chip for cancer cell capture, liquid sensors, and valves. The method includes: coupling a cut plane of one side of the cell separation cartridge to one side of the base plate; engaging a recess formed at the other end of the cell separation cartridge with a pin formed at the other end of the base plate; fixing holes of the separation chip of the cell separation cartridge and holes of the magnetic chip of the base plate using a fixing member to match the holes of the separation chip of the cell separation
(Continued)

cartridge and the holes of the magnetic chip of the base plate; and determining whether a pattern of the separation chip of the cell separation cartridge matches a pattern of the magnetic chip of the base plate.

19 Claims, 9 Drawing Sheets

(51) Int. Cl.
    *G01N 35/08*     (2006.01)
    *G01N 35/00*     (2006.01)

(52) U.S. Cl.
    CPC .............. *G01N 35/00* (2013.01); *G01N 35/08* (2013.01); *B01L 2200/0652* (2013.01); *B01L 2300/087* (2013.01); *B01L 2300/088* (2013.01); *B01L 2300/0816* (2013.01); *B01L 2300/0864* (2013.01); *B01L 2300/0877* (2013.01); *B01L 2400/043* (2013.01)

(58) Field of Classification Search
    CPC ....... B01L 2300/0877; B01L 2300/088; B01L 2400/043; B01L 3/502761; B01L 3/502776; G01N 33/574; G01N 35/00; G01N 35/08
    See application file for complete search history.

(56) References Cited

U.S. PATENT DOCUMENTS

2010/0123457 A1* 5/2010 Shinoda ............ B01L 3/502761
    324/228
2012/0322683 A1 12/2012 Liu
2013/0255361 A1 10/2013 Juncker et al.
2015/0151300 A1* 6/2015 Williams .......... B01L 3/502761
    435/5

FOREIGN PATENT DOCUMENTS

| | | |
|---|---|---|
| JP | 2009521684 A | 6/2009 |
| JP | 2015028497 A | 2/2015 |
| KR | 1020130095485 A | 6/2014 |
| KR | 1020140067888 A | 6/2014 |
| KR | 1020130142348 A | 5/2015 |
| KR | 1020150101985 B1 | 1/2016 |
| KR | 1020160019173 B1 | 10/2016 |
| WO | WO2003065042 A1 | 8/2003 |
| WO | WO2015058206 A1 | 4/2015 |
| WO | WO2015176744 A1 | 11/2015 |

OTHER PUBLICATIONS

Jeong Won Park et al; Microdevice for Separation of Circulating Tumor Cells Using Embedded Magnetophoresis with V-shaped Ni—Co Nanowires and Immuno-nanomagnetic Beads; ETRI Journal, vol. 37, No. 2, Apr. 2015; pp. 233-240; Daejeon, Korea.

International Search Report of PCT/KR2016/015502, English Translation, dated Feb. 27, 2017.

* cited by examiner

CELL SEPARATION CHIP AND SYSTEM

CROSS-REFERENCE TO RELATED APPLICATIONS

This application is the U.S. National Phase under 35 U.S.C. § 371 of International Application No. PCT/KR2016/015502 filed on Dec. 29, 2016, which in turn claims the benefit of Korean Applications No. 10-2016-0019173, filed on Feb. 18, 2016 and No. 10-2016-0182071, filed on Dec. 29, 2016, the disclosures of which are incorporated by reference into the present application.

TECHNICAL FIELD

The present invention relates to a system and method for cell separation. More specifically, the present invention relates to a system for cell separation in which an injection part and a separation part necessary for cell separation are provided on the same cartridge so that they can be coupled to and separated from each other by one-time operation and accurate coupling of the cell separation cartridge to a base plate can be easily checked, and a method for cell separation using the system.

BACKGROUND ART 27.9% of all deaths in Korea in 2015 resulted from cancer and the number thereof was 76,855. Cancer deaths are rising steadily every year. Lung cancer was the leading cause of cancer death in Korea and its rate was 17,399 in 2015. The rates of liver cancer, gastric cancer, and pancreatic cancer in both Korean men and women increase in this order. Most of these cancer patients do not die of their primary tumors but of metastases of a broad range of multiple tumor colonies formed by malignant cells that are separated from initial tumors and often migrate to distal sites through blood. Primary tumors detected in the initial stage can be removed by surgery, radiotherapy or chemotherapy but cancer cells circulating in the bloodstream are present at very low concentrations that are difficult to detect. For this reason, the likelihood of success of initial detection of cancer cells in blood is substantially low. Cancer cells in blood refer collectively to cancer cells present in the peripheral blood of cancer patients and are defined as cancer cells that fall off from primary or metastatic lesions. In recent years, approaches have been developed to use cancer cells in blood as potent biomarkers for cancer diagnosis, analysis of therapeutic prognosis, and analysis of micrometastasis. As described above, a very low concentration of cancer cells is distributed in blood. For example, one cancer cell is present per billion normal cells or one to ten million leukocytes in blood. Cancer cells are difficult to accurately analyze due to the presence of interfering factors such as contaminants and air bubbles during analysis. In addition, systems for separating cancer cells from blood are still relatively expensive given that the number of cancer patients is rapidly increasing every year. Most of such systems are disposable and are discarded after use. In addition to this economic burden, the systems are complicated to install.

Specifically, a method for separating cancer cells from blood involves three steps, i.e. blood sample production, sample injection, and cancer cell separation. The blood sample is prepared by mixing and binding blood, an antibody reacting specifically with cancer cells, and a functional material for downstream cancer cell separation such as a magnetic material. Then, the blood sample is injected into a system for cancer cell separation. It is important to inject an accurate amount of the blood sample at a constant flow rate while precluding the entrance of interfering factors, such as contaminants and air bubbles. The magnetic material previously bound to the blood is used as a carrier for cancer cell separation. The system usually includes a plurality of divided flow channels for cancer cells and non-cancer cells. It is important to secure accurate separation of cancer cells by maintaining the flow rates of the substances flowing through the flow channels at constant levels.

Many technologies for cancer cell separation have been investigated so far. Patent Document 1 relates to a method and reagent for rapidly and effectively separating circulating cancer cells and proposes a technique for separating cancer cells from a mixture of blood collected from a patent and a ligand (the can be detected due to its specific reaction with cancer cells). However, this patent document fails to consider the problems of contamination during injection of the blood sample and inaccurate separation of cancer cells. Patent Document 2 proposes a technique for separating cancer cells using ferromagnetic wires. However, this patent document fails to consider technical details for securing preset values for flow channels during discharge and the same amount and rate of substances flowing through the flow channels. Particularly, channels are usually used to accommodate separated cancer cells in a given container. At this time, the flow rate of the cancer cells in each flow channel may vary depending on the length and height of the channel, causing poor separation accuracy.

PRIOR ART DOCUMENTS

Patent Documents

1: International Patent Publication WO 2003/065042
2: Korean Patent Publication No. 2015-0058955

DETAILED DESCRIPTION OF THE INVENTION

Problems to be Solved by the Invention

The present invention has been made in an effort to solve the problems of the prior art, and one object of the present invention is to secure high accuracy of blood sample injection and cell separation by minimizing the entrance of contaminants A further object of the present invention is to provide a system for cell separation in which expensive or easy-to-recycle members are provided on the same cartridge or base plate so that they can be coupled to and separated from each other by one-time operation.

Another object of the present invention is to provide a system for cell separation in which accurate coupling between a cartridge and a base plate is previously checked to secure accurate cell separation when the cartridge is replaced with a new one.

Means for Solving the Problems

A cell separation system according to one aspect of the present invention includes: a cartridge having a polygonal shape in cross section and including an injection part, a separation chip separating a flow channel of a sample injected through the injection part, and a discharge part; and a base plate coupled to the cartridge through its upper surface and including a magnetic chip for cancer cell capture, liquid sensors, and valves.

The separation chip includes a top plate having holes into which pipes are insertable, each hole including a first portion having a larger diameter and a second portion having a smaller diameter. The separation chip includes a second member coupled to the top plate through a tape applied to the upper surface thereof and a first member located under the second member and coupled to the lower surface of the second member through a tape applied to the lower surface of the second member. Portions of the second member are cut-off to form channels in the second member, the holes are formed so as to penetrate through the upper and lower surfaces of the top plate and to be in communication with the channels, and the pipes are inserted into the first portions of the holes at acute angles to the upper surface of the top plate.

In the cell separation system of the present invention, the magnetic chip includes a wire pattern that is parabolic from one side to the other side thereof.

Particularly, the top plate of the separation chip of the cell separation system according to the present invention is made of a plastic.

The channels of the cell separation system according to the present invention include a first channel and a second channel in communication with the first channel and branched into a plurality of sub-channels, each of which includes a first portion and a second portion in communication with the first portion, the first portion being widened toward the second portion and the second portion being tapered toward a third channel in communication with the second channel.

The channels of the cell separation system according to the present invention include a first channel and a second channel in communication with the first channel, branched into a plurality of sub-channels, and having an arc shape.

The channels of the cell separation system according to the present invention include a first channel and a second channel in communication with the first channel and branched into a plurality of sub-channels, a plurality of protrusions being formed on the first channel or the second channel.

The protrusions include first protrusions and second protrusions underlying or adjacent to the first protrusions.

In the cell separation system of the present invention, filters are located on and in communication with the channels and have predetermined spaces.

In the cell separation system of the present invention, the channels of the discharge part of the cartridge are in contact with the liquid sensors and the valves when the cartridge is coupled to the base plate or the cell separation cartridge has a plane cut at a specific angle at one side thereof, the edge of the cut plane is higher than the lower surface of the cartridge, and the cartridge has a recess engaged with a pin at the other side thereof. The base plate has a plane formed at one side thereof to press the edge of the cut plane of the cartridge while in contact with the edge of the cut plane of the cartridge and connected from a position higher than the edge of the cut plane of the cartridge to a position lower than the edge, and includes a pin member provided at the other side thereof and engaged with the recess of the cartridge.

The pin member has the ability to always return to the central position and includes a protrusion horizontally rotatable at full 360°, both end edges of the coupling plane of the cartridge at one side where the cartridge is coupled to the base plate are cut at a predetermined angle, and both end edges of the coupling plane of the base plate facing the coupling plane of the cartridge are cut at the same angle such that both end edges of the coupling plane of the cartridge match and are coupled to the both end edges of the coupling plane of the base plate.

The separation chip of the cartridge of the cell separation system according to the present invention has a polygonal shape in cross section is patterned at a predetermined position and includes holes matching the magnetic chip of the base plate at one or more edges thereof. The magnetic chip of the base plate has a polygonal shape in cross section, is patterned at a predetermined position, and includes holes matching the separation chip of the cartridge at one or more edges thereof. The distances between the magnetic chip of the base plate and the holes and the pattern formed in the magnetic chip are the same as those between the separation chip of the cartridge and the holes and the pattern formed in the separation chip. Here, the base plate and the cartridge have the same shape and the same number of the holes or the pattern on the cartridge matches the pattern on the base plate.

A method for cell separation according to a further aspect of the present invention uses the cell separation system. Specifically, the method includes: fixing the separation chip to the cell separation cartridge and fixing the magnetic chip to the base plate; coupling the cut plane of one side of the cell separation cartridge to one side of the base plate; engaging the recess formed at the other end of the cell separation cartridge with the pin formed at the other end of the base plate; and confirming whether the holes of the separation chip of the cartridge match the holes of the magnetic chip of the base plate.

Effects of the Invention

In the system and method for cell separation according to the present invention, the injection part and the separation part necessary for cell separation are provided on the same cartridge so that they can be coupled to and separated from each other by one-time operation and accurate coupling of the setting can be checked.

In addition, a group of easy-to-replace members and a group of difficult-to-replace members are separately provided on the same cartridge or plate. This construction is effective in improving the reuse efficiency of the cell separation system.

Particularly, the separation chip of the cell separation system according to the present invention is made of a plastic that can be wasted after completion of examination. Therefore, the separation chip does not need to be washed. The separation chip can be produced by a relatively simple technique rather than by a semiconductor technique or MEMS technique, which contributes to production cost saving. In addition, the separation chip can be produced on a large scale, securing economic efficiency while ensuring constant quality.

MODE FOR CARRYING OUT THE INVENTION

A system and method for cell separation according to the present invention will now be described with reference to the accompanying drawings.

In the present application, it is to be understood that the terms such as "including" or "having," etc., are intended to indicate the existence of the features, numbers, steps, elements, parts, or combinations thereof disclosed in the specification, and are not intended to preclude the possibility that one or more other features, numbers, steps, elements, parts, or combinations thereof may exist or may be added.

Unless otherwise defined, all terms used herein, including technical or scientific terms, have the same meanings as those generally understood by those with ordinary knowledge in the field of art to which the present invention belongs. Such terms as those defined in a generally used dictionary are to be interpreted to have the meanings equal to the contextual meanings in the relevant field of art, and are not to be interpreted to have ideal or excessively formal meanings unless clearly defined in the present application.

Figure 1:
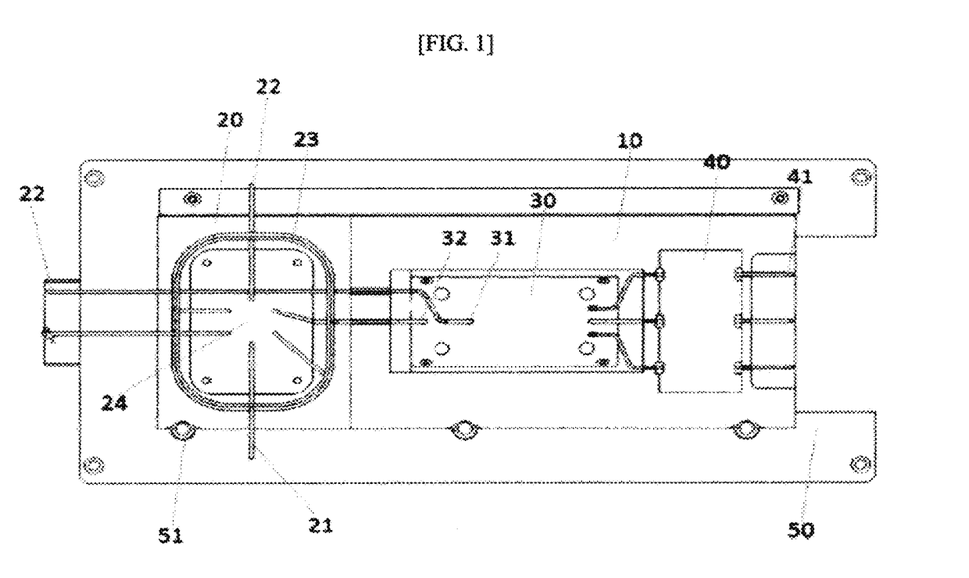
FIG. 1 is a top cross-sectional view of a cell separation system according to one embodiment of the present invention.

FIG. 1 illustrates a top cross-sectional view of a cell separation system according to one embodiment of the present invention. Referring to FIG. 1, the cell separation system consists essentially of a cartridge 10 and a base plate 50. The cartridge 10 has a polygonal shape in cross section and includes an injection part 20 and a separation chip 30. Blood, a sample bound with a functional additive for downstream separation and a buffer solution enter through the injection part 20. To this end, the injection part 20 has three inlet ports 21 and 22, as illustrated in FIG. 1. Care should be taken to avoid the entrance of contaminants during injection. In addition, constant amounts of the blood, the functional additive, and the buffer solution should be always injected at constant flow rates. The entrance of an interfering substance other than the blood, the functional additive, and the buffer solution may produce errors in subsequent analysis. As described above, since only a very small amount of cancer cells is present in blood, the entrance of a small amount of an interfering substance may cause significant errors in analysis results. Changes in the flow rates or the amounts of the substances injected may lead to changes in the rates of the substances flowing through flow channels in a downstream separation step, increasing the possibility of errors during separation. Thus, as illustrated in FIG. 1, a sample loop 23 having a predetermined volume is interposed between the injection part 20 and the downstream separation chip 30 such that the amount and flow rate of the sample injected are maintained constant. In the cell separation system, the separation chip 30 is located downstream of the injection part 20 to separate cancer cells. The injection part 20 is interconnected to the separation chip 30 through the sample loop 23 or general channels. The separation chip 30 receives the sample and the buffer solution from the injection part 20 through two channels 31 and 32 connected to the injection part 20.

Figure 2:
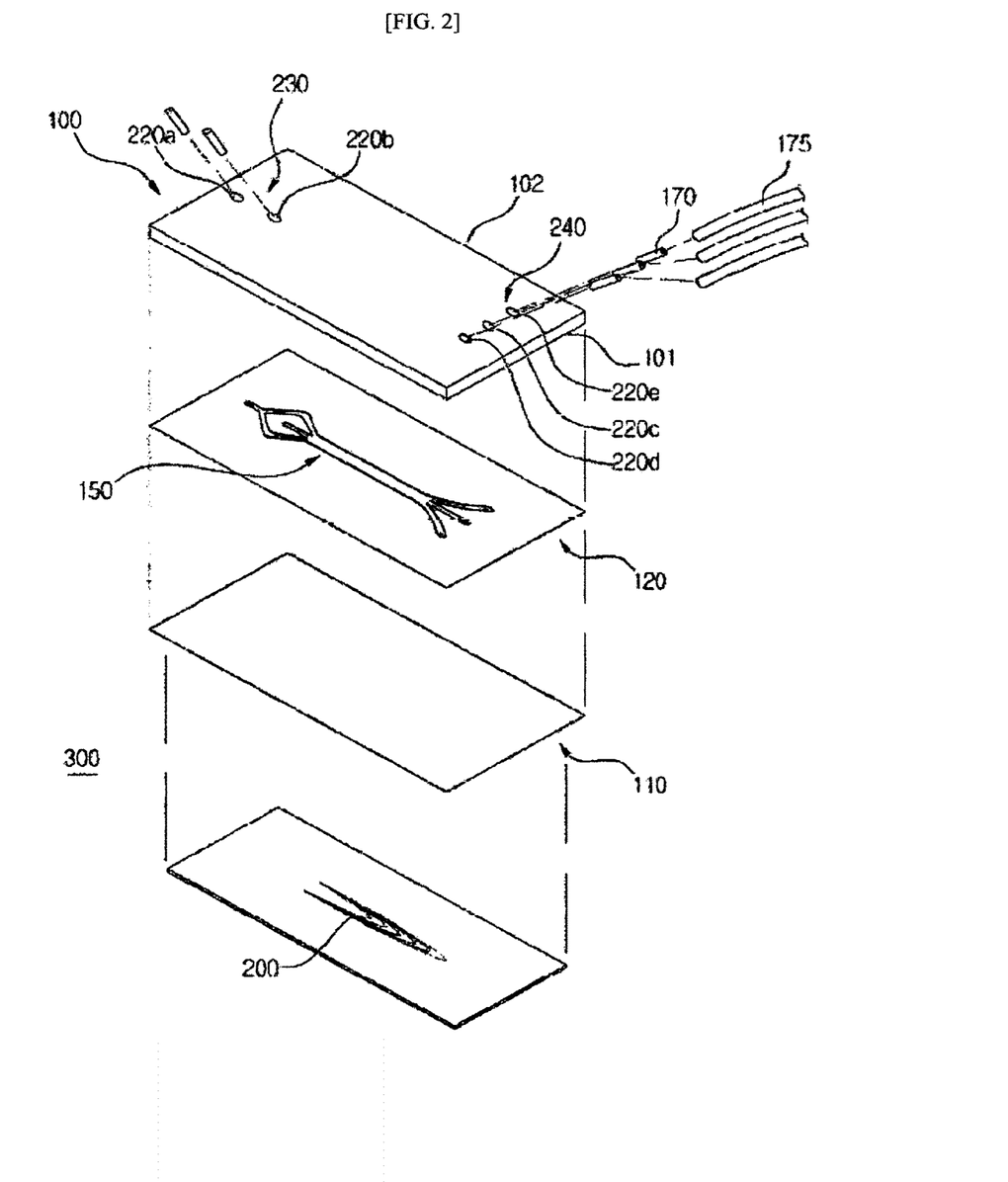
FIG. 2 illustrates a first embodiment of a separation chip 30 according to one embodiment of the present invention.

In the present invention, a magnetic material bound to an antibody reacting specifically with cancer cells is used to separate the cancer cells. Cancer cells in blood are bound to the magnetic material during mixing with the blood. To this end, the separation chip 30 of the cartridge 10 is separably coupled to a magnetic chip 35 of the base plate 50. Due to this construction, the separation chip 30 made of a plastic can be wasted after one-time use. FIG. 2 illustrates one embodiment of the separation chip 30 of the cell separation system according to the present invention. Referring to FIG. 2, the separation chip 30 consists of a top plate, a first member, and a second member. The magnetic chip 35 is coupled to the bottom of the separation chip 30.

First, the construction of the separation chip 30 will be discussed. The shape of the top plate 100 is similar to that of a thin rectangular plate. The first member 110 is similar to a plate whose thickness is smaller than its length and width. The top plate 100 is coupled to the first member 110. Here, the second member 120 is interposed between the top plate 100 and the first member 110. The thickness of the second member 120 is designed to be smaller than the length and width thereof. The separation chip 30 of the cell separation system uses a double-sided adhesive tape as the second member 120. Accordingly, the top plate 100 is coupled to the first member 110 by an adhesive applied to the upper and lower surfaces of the second member 120.

A plurality of holes are formed in the separation chip 30. Specifically, a hole 220a through which a sample solution is introduced and a hole 220b through which the buffer solution such as saline is introduced are formed at one side of the top plate 100. A hole 220c through which magnetic bead-bound cells are discharged and holes 220d and 220e through which other materials are discharged are formed at the other side of the top plate 100. The plurality of holes are in communication with the channels and pipes 170 are inserted into the holes.

The magnetic chip 35 of the cell separation system is smaller in length and width than the separation chip 30, as illustrated in FIG. 1. A wire-shaped magnetic chip pattern 200 is parabolic from one side to the other side of the magnetic chip 35. Specifically, the wire pattern 200 is located from the starting point of a third channel 153, one of the channels 150, where cells are separated, to the end point of the third channel 153. That is, the vertex of the parabolic wire pattern 200 is formed close to the end point of the third channel 153.

The separation chip 30 of the cell separation system may be made of a plastic. Specifically, one or more of the top plate 100, the first member 110, and the second member 120 may be made of a plastic. Any plastic polymer may be used for the separation chip 30. Polycarbonate is preferred because its transparency and strength are above predetermined levels.

Figure 3:
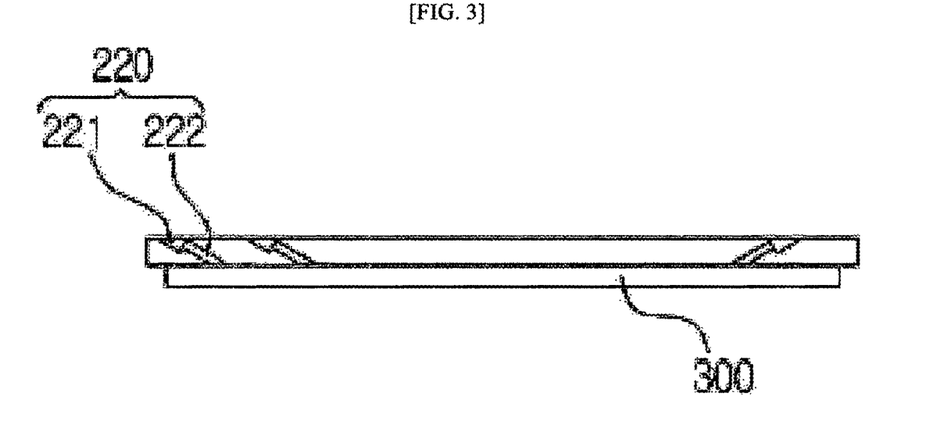
FIG. 3 illustrates the construction of holes of a separation chip 30 according to one embodiment of the present invention.

Unlike in the prior art, the channels are not directly connected to the separation chip 30 of the cell separation system but are connected to the separation chip 30 of the cell separation system through the pipes, as described above. For these connections, the diameters of the holes 220 formed in the top plate 100 and in communication with the channels 150 vary depending on the lengths of the channels. FIG. 3 illustrates the construction of the holes of the separation chip 30 of the cell separation system. Referring to FIG. 3, each of the holes consists of a first portion 221 and a second portion 222. The first portion 221 has a relatively large diameter compared to the second portion 222. With these dimensions, the pipes 170 can be inserted into the corresponding holes. The number of the holes 220 formed when the top plate 100 is coupled to the second member 120 may vary depending on the total number of the introduction holes formed at one side of the separation chip 30 and the discharge holes formed at the other side of the separation chip 30. When a solution is directly introduced into a channel without using a pipe, as in the prior art, the rate of the solution introduced into a hole may be rather unstable. The channel may also be displaced when the separation chip is handled by an unskilled user. In contrast, since the pipes 170 are inserted into the holes 220a to 220e and solutions flow from tubes 175 into the channels 150 via the pipes 170, the separation chip 30 ensures stable introduction/flow of the solutions into/in the channels. The separation chip 30 is constructed such that the pipes 170 are inserted at acute angles to the upper surface 102 of the top plate. For this construction, the holes 220a to 220e are inclined at acute angles to the upper surface 102 of the top plate. In this case, the pipes 170 inserted into the holes 220a to 220e also form acute angles to the upper surface 102 of the top plate. According to the prior art, solutions are introduced into channels through syringes. In this case, the introduction holes are at right angles or substantially right angles to the syringes. The large angles relative to the injection lines lead to an increase in injection pressure, and as a result, smooth flows of the solutions are not ensured, increasing the probability of cell retention. In contrast, according to the cell separation system of the present invention, the acute angles between the pipes inserted into the holes and the upper surface of the top plate lead to low flow resistance, and as a result, smooth flows of the solutions are ensured, decreasing the probability of cell retention and improving the durability of the chip. According to the prior art, solutions are injected in the vertical direction through introduction holes or discharge holes. In this case, when a lens moves for close observation of the introduction holes or the discharge holes, interference may be caused by tubes in communication with channels and made of a synthetic rubber such as PDMS. In contrast, the use of the pipes in the cell separation system of the present invention and the connection of the pipes to the introduction holes and the discharge holes at acute angles rather than at right angles facilitate observation in the introduction holes 230 or the discharge holes 240 and prevent interference with the tubes 175 when a lens is focused on the introduction holes 230 or the discharge holes 240, enabling easy observation of the solution flows.

Figure 4:
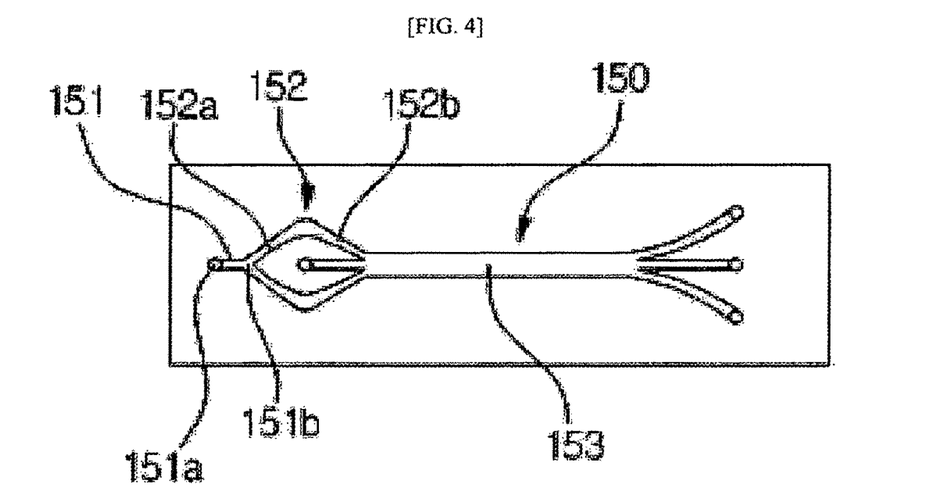
FIG. 4 illustrates a first embodiment of channels of a separation chip 30 according to one embodiment of the present invention.
Figure 5:
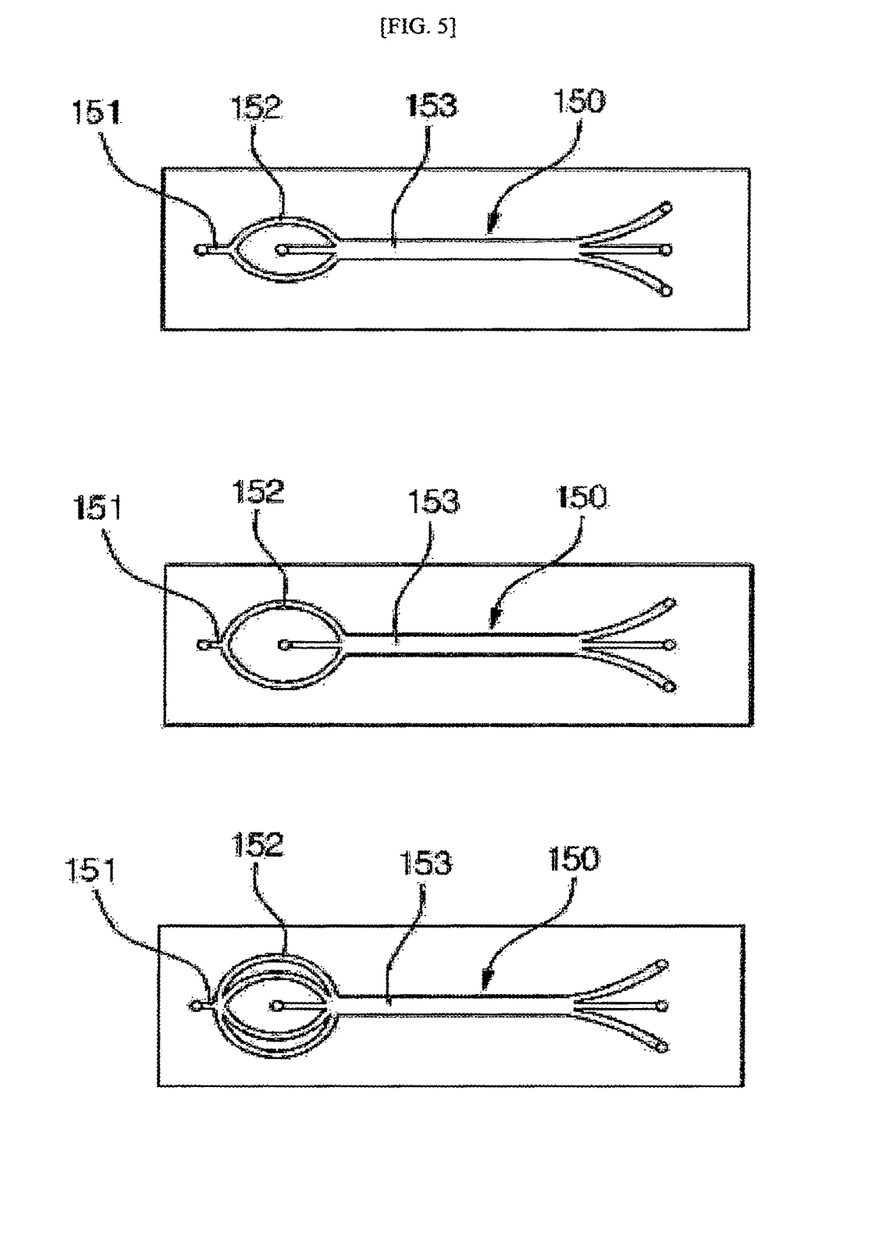
FIG. 5 illustrates a second embodiment of channels of a separation chip 30 according to one embodiment of the present invention.
Figure 6:
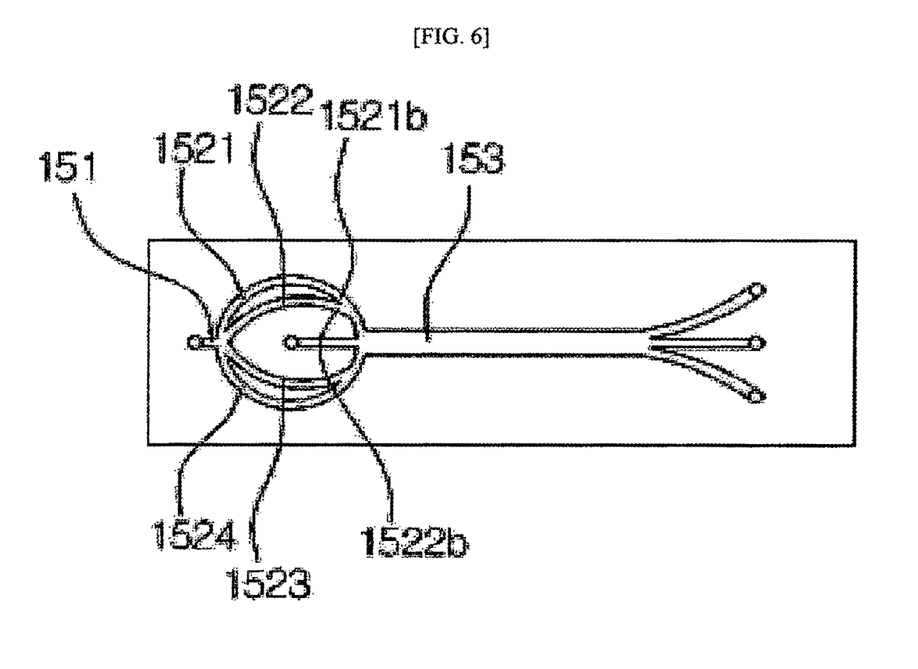
FIG. 6 illustrates a third embodiment of channels of a separation chip 30 according to one embodiment of the present invention.

In the separation chip 30 of the cell separation system, the channels may be embodied in various different forms. FIG. 4 illustrates a first embodiment of the channels. Referring to FIG. 4, a first channel 151 in communication with the introduction hole 220a is located in the middle of the top plate 100 in the widthwise direction of the top plate 100 and is formed at one side of the top plate 100 in the lengthwise direction of the top plate 100. One side 151a of the first channel may be in communication with the introduction hole 220a and the other side 151b of the first channel is in communication with a second channel 152. The second channel 152 includes a plurality of branched sub-channels. The following description will be given mainly on the overlying branched sub-channels in the widthwise direction of the top plate 100. First, each of the branched sub-channels includes a first portion 152a and a second portion 152b. The first portion 152a of the branched sub-channel extends upward from the first channel 151 in the right direction and has a predetermined length. The second portion 152b of the branched sub-channel is in communication with the first portion 152a of the branched sub-channel. The second portion 152b of the branched sub-channel extends downward from the other side of the first portion 152a of the branched sub-channel and has a predetermined length. The first portion 152a of the branched sub-channel is widened toward the second portion 152b of the branched sub-channel. In contrast, the second portion 152b of the branched sub-channel is tapered from the other side of the first portion 152a of the branched sub-channel toward a third channel 153 in communication with the second portion 152b of the branched sub-channel. That is, the portion of the branched sub-channel where the other side of the first portion 152a is connected to the one side of the second portion 152b is bent such that a flow of a solution is changed and is widened such that cells in the solution spread widely throughout the entire channel ("redistribution effect") based on the vortex flow. If the width of the branched sub-channel is maintained constant, cells flow along only one wall of the channel after passage through the bent portion where the other side of the first portion 152a of the branched sub-channel is connected to the one side of the second portion 152b. FIG. 5 illustrates a second embodiment of the channels of the separation chip 30 of the cell separation system. As well illustrated in FIG. 5, a first channel 151 in communication with the introduction hole 220a formed at one side of the top plate 100 is located in the middle of the top plate 100 in the widthwise direction of the top plate 100 and is formed at one side of the top plate 100 in the lengthwise direction of the top plate 100. For reference, the first channel 151 is smaller in length than a second channel 152 in communication with the first channel 151. The second channel 152 includes a plurality of branched sub-channels. As illustrated in FIGS. 5 and 6, the second channel 152 may have an arc shape. The second channel 152 is located above and below the middle of the top plate 100 in the widthwise direction of the top plate 100 and may be branched into a plurality of sub-channels. The number of the branched sub-channels above the middle of the top plate 100 in the widthwise direction of the top plate 100 is at least two and the number of the branched sub-channels below the middle of the top plate 100 in the widthwise direction of the top plate 100 is at least two.

A third embodiment of the channels of the separation chip 30 of the cell separation system according to the present invention is illustrated in FIG. 6. The separation chip 30 includes a plurality of branched sub-channels of a second channel 152 at one side of the top plate 100. Some of the branched sub-channels are combined into one before in communication with a third channel 153. The branched sub-channels are located above and below the middle of the top plate 100 in the widthwise direction of the top plate 100. The number of the branched sub-channels above the middle of the top plate 100 in the widthwise direction of the top plate 100 is two and the number of the branched sub-channels below the middle of the top plate 100 in the widthwise direction of the top plate 100 is two. In the following description, the two branched sub-channels located above the middle of the top plate 100 in the widthwise direction of the top plate 100 are defined as a $2\text{-}1^{st}$ channel 1521 and a $2\text{-}2^{nd}$ channel 1522 and the two branched sub-channels located below the middle of the top plate 100 in the widthwise direction of the top plate 100 are defined as a $2\text{-}3^{rd}$ channel 1523 and a $2\text{-}4^{th}$ channel 1524. A portion of the $2\text{-}1^{st}$ channel 1521 and a portion of the $2\text{-}2^{nd}$ channel 1522 are combined to form one channel before in communication with the third channel 153. Specifically, the portion 1521b of the $2\text{-}1^{st}$ channel 1521 is adjacent to the third channel 153 and the portion 1522b of the $2\text{-}2^{nd}$ channel 1522 is adjacent to the third channel 153. The portion 1521b of the $2\text{-}1^{st}$ channel and the portion 1522b of the $2\text{-}2^{nd}$ channel are combined into one and are in communication with the third channel 153.

Figure 7:
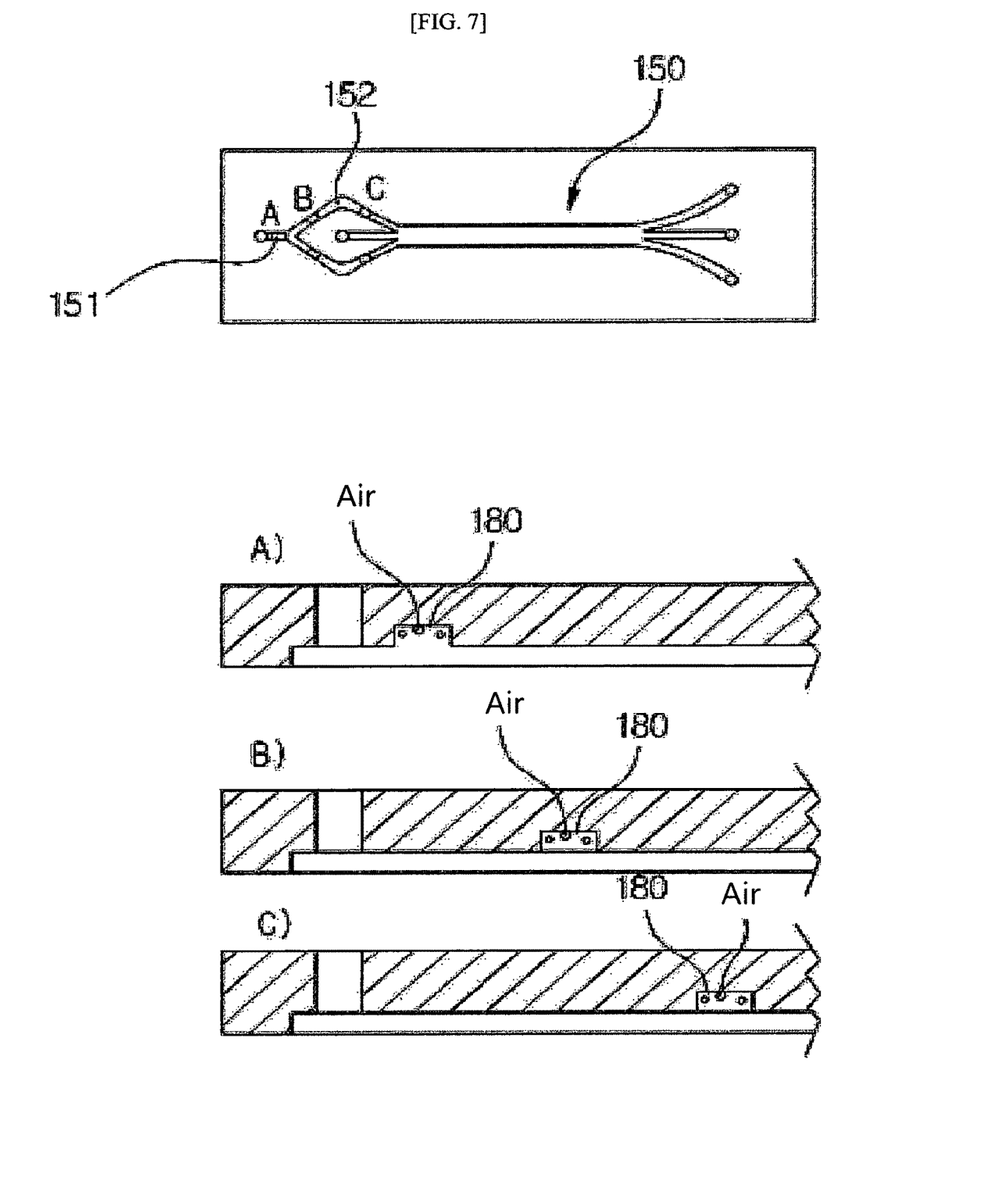
FIG. 7 illustrates the locations of filters on channels of a separation chip 30 according to one embodiment of the present invention.
Figure 8:
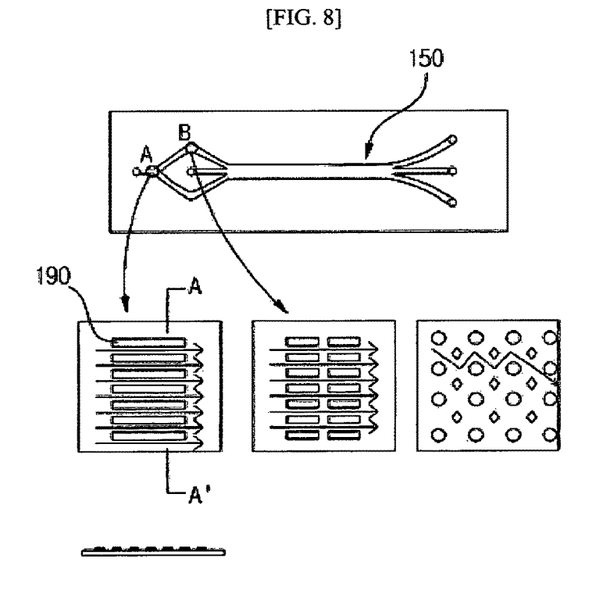
FIG. 8 illustrates the construction of filters of a separation chip 30 according to one embodiment of the present invention.

The separation chip 30 of the cell separation system according to the present invention may include filters located on the channels. Referring to FIG. 7, a filter is located on the first channel 151 or the second channel 152 of the separation chip 30. The filter 180 may be provided in plurality on the second channel 152. Specifically, one filter 180 may be located on the first portion 152a of the second channel and one filter 180 may be located on the second portion 152b of the second channel. It should be understood that one or more filters 180 may also be located on the first channel 151. The filters 180 are in communication with the channels 150 and have predetermined spaces. In the cell separation system of the present invention, the filters serve to remove gases (air) present in a solution flowing in the channels. When a gas-containing solution passes through the filters 180, the gases float above the solution due to their different specific gravities. The gases are confined in the spaces of the filters 180 in communication with the channels 150. The collected gases are removed from the solution. The arrangement of the filters on the channels of the separation chip 30 of the cell separation system according to the present invention is illustrated in FIG. 7. As illustrated in FIG. 7, the filters 180 are located on the channels 150. As illustrated in FIG. 8, protrusions 190 may be formed in the separation chip 30. As illustrated in FIG. 7, the second channel 152 is in communication with the first channel 151 and is branched into a plurality of sub-channels. The protrusions 190 are formed on the first channel 151 or the second channel 152. The protrusions 190 are located on the second member 120 in which the channels 150 are formed. The channels 150 are formed by cutting off portions of the second member 120 along the shapes of the channels 150, which has been previously described. Here, the protrusions 190 are formed on the channels 150 by cutting off portions other than the portions occupied by the protrusions 190 in the width direction of the channel 150. The protrusions 190 are slightly higher than the cut-off portions. The distances between the adjacent protrusions 190 are designed to be smaller than the size of air particles mixed in the solution. When the solution is introduced into the channels 150, the protrusions can prevent air particles mixed in the solution from flowing into the channels 150. The shape of the protrusions 190 is not limited as long as the protrusions 190 can filter air particles. For example, the protrusions 190 may be rectangular, circular or diamond in shape. The protrusions 190 formed on the first channel 151 or the second channel 152 may also be arranged in one or more rows. That is, the protrusions 190 may include first protrusions A and second protrusions B underlying or adjacent to the first protrusions A, as illustrated in FIG. 8.

Cancer cells separated by the separation chip 30 and the magnetic chip 35 and blood free of cancer cells are accommodated in separate containers. In this course, the cancer cells and the blood are usually discharged through the simply connected channels. However, the use of the channels affects the internal pressure of each flow channel of the upstream separation unit. That is, when it is desired to separate cancer cells and a blood sample free of cancer cells, the rates and amounts of the substances flowing through the flow channels should be constant for accurate separation. If large amounts of the substances flow through some of the flow channels or the substances flow at high rates, the substances are concentrated on only the particular flow channels, causing errors in the separation of cancer cells. If the heights of the channels connected to external containers are not the same and the lengths of the channels are different, the rates and amounts of the substances flowing through the flow channels vary. To solve these problems, the cell separation system of the present invention further includes a discharge part 40 (FIG. 1), liquid sensors 60, and valves 70 provided downstream of the separation chip 30. The liquid sensors 60 and valves 70 serve to previously detect the inflow of air bubbles during discharge and adjust the flow of the substances.

Figure 9:
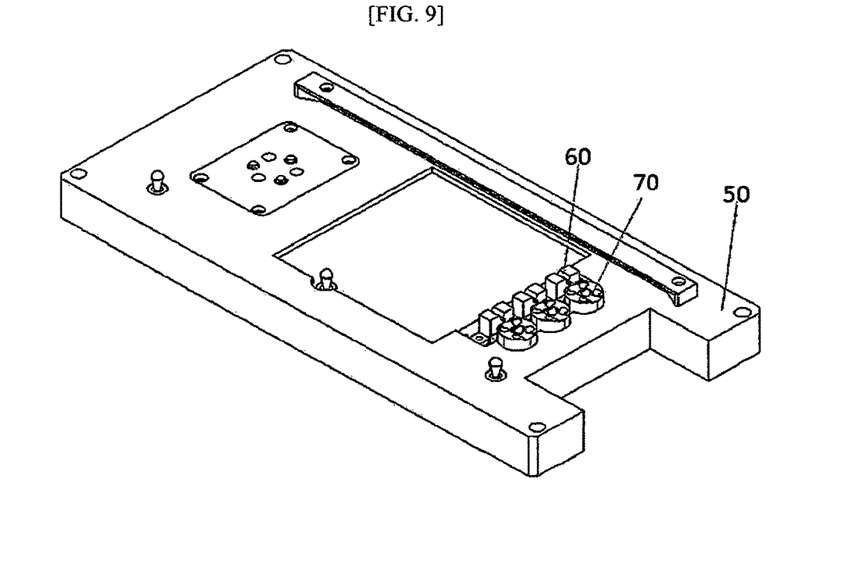
FIG. 9 is a top cross-sectional view of a base plate according to one embodiment of the present invention.

The important considerations in the spirit of the cell separation system according to the present invention are economic efficiency and convenience. The cell separation system is designed such that the cartridge 10 is separably coupled to the base plate 50 instead of integrating the two elements into one unit. Due to this design, disposable elements are distinguished from reusable elements. That is, the cartridge 10 of the cell separation system according to the present invention consists of the injection part 20, the separation chip 30, and the discharge part 40, which are disposable elements. In contrast, the magnetic chip 35 provided in the base plate 50 and the liquid sensors 60 and the valves 70 of the discharge part 40 are reusable elements. The cartridge 10 is coupled to the upper surface of the base plate 50. Here, the liquid sensors 60 and the valves 70 located on the upper surface of the base plate 50 come into contact with the discharge channels formed on the lower surface of the cartridge 10, as illustrated in FIG. 9. Due to this construction, the presence of air bubbles can be checked and the amounts of the substances flowing through the channels can be adjusted during discharge.

Figure 10:
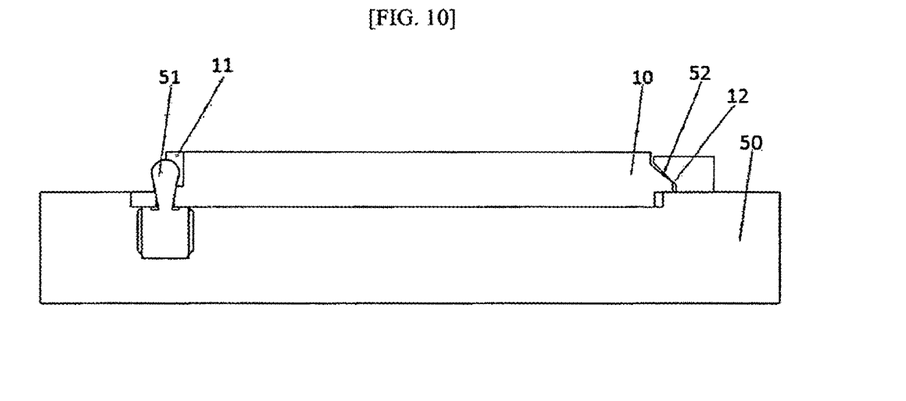
FIG. 10 is a cross-sectional view illustrating an arrangement in which a cell separation cartridge and a base plate are fixed to each other according to one embodiment of the present invention.

In the cell separation system of the present invention, the cartridge 10 is separably coupled to the base plate 50 after one-time use, as described above. Thus, the mechanism of separable coupling of these elements is important. To this end, the cell separation system of the present invention has a characteristic structure for coupling the cartridge 10 to the base plate 50. First, the cartridge 10 has a plane cut obliquely at a specific angle at one side thereof and has a recess 11 engaged with a pin 51 at the other side thereof, as illustrated in FIGS. 1 and 10. The base plate 50 is adapted for the cartridge 10. The base plate 50 has a cut coupling plane 52 formed at one side thereof to press and fix the obliquely cut plane of the cartridge 10. The pin 51 is provided at the other side of the base plate 50 and is engaged with the recess 11 of the cartridge 10. A more detailed description will be given with reference to FIG. 10. The coupling plane 52 formed at one side of the base plate 50 is connected from a position higher than an edge 12 of the cut plane of the cartridge 10 to a position lower than the edge 12 while in contact with the edge 12 so as to press the edge 12. The pin member 51 provided at the other side of the base plate 50 can be engaged with the recess 11 of the cartridge 10. Any pin member that can be connected to the recess 11 may be used. Preferably, the pin is thrust when the recess 11 of the cartridge 10 is pushed toward the pin for engagement and is returned to its original position to again fix the recess. Accordingly, in one embodiment of the present invention, a side thrust pin is used that has a protrusion horizontally rotatable at full 360° and is capable of always returning to the central position.

Figure 11:
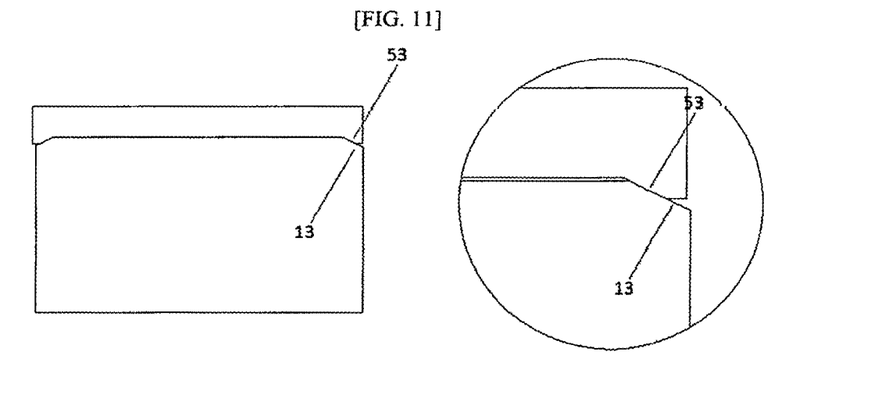
FIG. 11 illustrates a structure in which a cell separation cartridge is fixed to a base plate according to one embodiment of the present invention.

The cell separation system of the present invention uses inexpensive elements to construct the cartridge 10 and difficult-to-reuse elements to construct the base plate 50, as described above. Due to these constructions, the cartridge 10 is separated from the base plate 50 and is wasted after one-time use. Thereafter, a new cartridge 10 is coupled to the base plate 50. Accordingly, the new cartridge 10 should be accurately coupled to the base plate 50 for cancer cell separation. Specifically, the cancer cell flow channel formed in the separation chip 30 separating the sample flow channel of the cartridge 10 should accurately match the magnetic chip 35 provided in the base plate 50, and the liquid sensors 60 and the valves 70 provided on the base plate 50 should be coupled to each other such that the channels of the discharge part 40 provided in the cartridge 10 can be measured and controlled. To accurately implement this, the cell separation system of the present invention includes two technical features. According to the first feature, both widthwise ends of the interface where the cartridge 10 is coupled to the base plate 50 are cut at the same angle to form planes 13 and 53. The formation of the cut planes enables accurate coupling between the cartridge 10 and the base plate 50. This feature will be described in detail with reference to FIG. 11. The planes 13 are formed by cutting both widthwise ends of one side of the cartridge 10 coupled to the base plate 50 at a predetermined angle and the planes 53 are formed by cutting both widthwise ends of the side of the base plate 50 facing the one side of the cartridge 10 at the same angle. Due to this feature, the cartridge 10 is engaged with the base plate 50. When the cartridge 10 and the base plate 50 are cut at the same angle, both ends of the cartridge 10 naturally and accurately match both ends of the base plate 50, enabling engagement of the cartridge 10 with the base plate 50.

Figure 12:
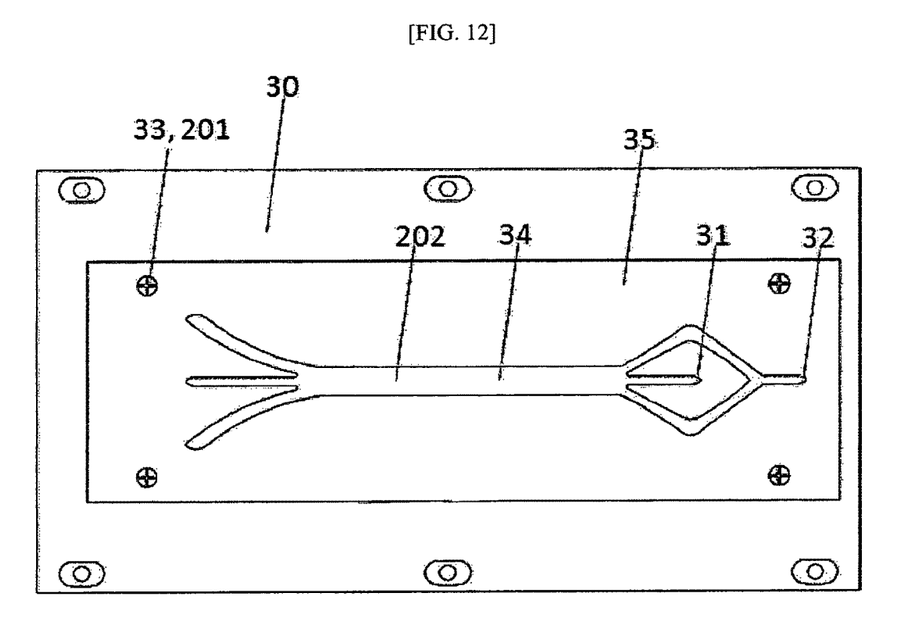
FIG. 12 illustrates a structure in which a separation chip 30 on a cartridge is coupled to a magnetic chip on a base plate.

According to the second feature, holes 33 and a pattern 34 formed on the separation chip 30 of the cartridge 10 match holes 201 and a pattern 202 formed on the magnetic chip 35 of the base plate 50. Referring to FIG. 12, the separation chip 30 of the cartridge 10 has a polygonal shape in cross section, is patterned at a predetermined position, and includes holes 33 matching the magnetic chip 35 of the base plate 50 at one or more edges thereof. The magnetic chip 35 of the base plate 50 has a polygonal shape in cross section, is patterned at a predetermined position, and includes holes 201 matching the separation chip 30 of the cartridge 30 at one or more edges thereof. The distances between the magnetic chip 35 of the base plate 50 and the holes 201 and the pattern 202 formed in the magnetic chip are the same as those between the separation chip 30 of the cartridge 10 and the holes 33 and the pattern 34 formed in the separation chip. Thus, when the cartridge 10 is coupled to the base plate 50, the holes 33 formed in the separation chip 30 of the cartridge 10 accurately match the holes 201 formed in the magnetic chip 35 of the base plate 50 such that the separation chip 30 and the magnetic chip 35 accurately match each other. To confirm whether the separation chip 30 accurately matches the magnetic chip 35 after coupling of the cartridge 10 to the base plate 50, a determination is made as to whether the pattern 34 formed in the separation chip 30 and the pattern 202 formed in the magnetic chip 35 match each other. To this end, it is preferred that the cartridge 10 and the base plate 50 have the same shape and the same number of the holes or the pattern on the cartridge 10 matches the pattern on the base plate 50.

The present invention also provides a method for cell separation using the cell separation system. The method includes: fixing the separation chip 30 to the cell separation cartridge 10 and fixing the magnetic chip 35 to the base plate 50; coupling the cut plane of one side of the cell separation cartridge 10 to one side of the base plate 50; engaging the recess 11 formed at the other end of the cell separation cartridge 10 with the pin 51 formed at the other end of the base plate; confirming whether the holes 33 of the separation chip 30 of the cartridge 10 match the holes 201 of the magnetic chip 35 of the base plate 50; and confirming whether the pattern 34 of the separation chip 30 of the cartridge 10 matches the pattern 202 of the magnetic chip 35 of the base plate 50.

Although the particulars of the present disclosure have been described in detail, it will be obvious to those skilled in the art that such particulars are merely preferred embodiments and are not intended to limit the scope of the present disclosure. Those skilled in the art will readily recognize and appreciate that various modifications and variations are possible without departing from the scope and spirit of the invention. Accordingly, such modifications and variations are intended to come within the scope of the appended claims.

The invention claimed is:

1. A cell separation system comprising: a cartridge having a polygonal shape in cross section and comprising an injection part, a separation chip separating a flow channel of a sample injected through the injection part, and a discharge part; a base plate coupled to the cartridge through its upper surface and comprising a magnetic chip for cancer cell capture, liquid sensors, and valves, wherein the separation chip comprises a second member coupled to a top plate of the cartridge through a tape applied to the upper surface thereof and a first member located under the second member and coupled to the lower surface of the second member through a tape applied to the lower surface of the second member; portions of the second member are cut-off to form channels in the second member; the holes are formed so as to penetrate through the upper and lower surfaces of the top plate and to be in communication with the channels; and the pipes are inserted into the first portions of the holes at acute angles to the upper surface of the top plate.

2. The cell separation system according to claim 1, wherein the top plate comprises holes into which pipes are insertable, each hole comprising a first portion having a larger diameter and a second portion having a smaller diameter.

3. The cell separation system according to claim 1, wherein the magnetic chip comprises a wire pattern that is parabolic from one side to the other side thereof.

4. The cell separation system according to claim 1, wherein the top plate is made of a plastic.

5. The cell separation system according to claim 1, wherein the channels comprise a first channel and a second channel in communication with the first channel and branched into a plurality of sub-channels, each of which comprises a first portion and a second-portion in communication with the first portion, the first portion being widened toward the second portion and the second portion being tapered toward a third channel in communication with the second channel.

6. The cell separation system according to claim 1, wherein the channels comprise a first channel and a second channel in communication with the first channel, branched into a plurality of sub-channels, and having an arc shape.

7. The cell separation system according to claim 1, wherein the channels comprise a first channel and a second channel in communication with the first channel and branched into a plurality of sub-channels, a plurality of protrusions being formed on the first channel or the second channel.

8. The cell separation system according to claim 7, wherein the protrusions comprise first protrusions and second protrusions underlying or adjacent to the first protrusions.

9. The cell separation system according to claim 1, wherein filters are located on the channels.

10. The cell separation system according to claim 9, wherein the filters are in communication with the channels and have predetermined spaces.

11. The cell separation system according to claim 1, wherein the channels of the discharge part of the cartridge are in contact with the liquid sensors and the valves when the cartridge is coupled to the base plate.

12. The cell separation system according to claim 1, wherein the cell separation cartridge has a plane cut at a specific angle at one side thereof, the edge of the cut plane is higher than the lower surface of the cartridge, and the cartridge has a recess engaged with a pin at the other side thereof.

13. The cell separation system according to claim 12, wherein the base plate has a plane formed at one side thereof to press the edge of the cut plane of the cartridge while in contact with the edge of the cut plane of the cartridge and connected from a position higher than the edge of the cut plane of the cartridge to a position lower than the edge, and includes a pin member provided at the other side thereof and engaged with the recess of the cartridge.

14. The cell separation system according to claim 13, wherein the pin member has the ability to always return to the central position and comprises a protrusion horizontally rotatable at full 360°.

15. The cell separation system according to claim 12, wherein both end edges of the coupling plane of the cartridge at one side where the cartridge is coupled to the base plate are cut at a predetermined angle, and both end edges of the coupling plane of the base plate facing the coupling plane of the cartridge are cut at the same angle such that both end edges of the coupling plane of the cartridge match and are coupled to the both end edges of the coupling plane of the base plate.

16. The cell separation system according to claim 1, wherein the separation chip of the cartridge has a polygonal shape in cross section and is patterned at a predetermined position, and comprises holes matching the magnetic chip of the base plate at one or more edges thereof.

17. The cell separation system according to claim 16, wherein the magnetic chip of the base plate has a polygonal shape in cross section, is patterned at a predetermined position, and comprises holes matching the separation chip of the cartridge at one or more edges thereof; and the distances between the magnetic chip of the base plate and the holes and the pattern formed in the magnetic chip are the same as those between the separation chip of the cartridge and the holes and the pattern formed in the separation chip.

18. The cell separation system according to claim 17, wherein the holes of the magnetic chip are the same as the holes of the separation chip in shape and number, or the pattern of the magnetic chip is matched with the pattern of the separation chip.

19. A method for cell separation comprising: coupling a cut plane of one side of a cell separation cartridge to one side of a base plate; engaging a recess formed at the other end of the cell separation cartridge with a pin formed at the other end of the base plate; and confirming whether holes of a separation chip of the cartridge match holes of a magnetic chip of the base plate.

* * * * *